(12) United States Patent  
Ames et al.

(10) Patent No.: US 8,409,087 B2
(45) Date of Patent: Apr. 2, 2013

(54) EXPANDABLE RETRACTOR AND METHODS INCORPORATING THE SAME

(75) Inventors: Christopher Ames, San Francisco, CA (US); Gregory Causey, Erie, CO (US)

(73) Assignee: Lanx, Inc., Broomfield, CO (US)

( * ) Notice: Subject to any disclaimer, the term of this patent is extended or adjusted under 35 U.S.C. 154(b) by 43 days.

(21) Appl. No.: 12/759,539

(22) Filed: Apr. 13, 2010

(65) Prior Publication Data

US 2011/0034777 A1   Feb. 10, 2011

Related U.S. Application Data

(60) Provisional application No. 61/168,758, filed on Apr. 13, 2009.

(51) Int. Cl.
*A61B 17/70* (2006.01)
*A61B 17/66* (2006.01)
*A61B 1/32* (2006.01)

(52) U.S. Cl. .................. 600/210; 606/105; 600/225

(58) Field of Classification Search .......... 600/201–219, 600/224–225; 606/90, 96, 99, 104, 86 A, 606/86 B, 280–282, 105; *A61B 1/32, 17/66, A61B 17/70*
See application file for complete search history.

(56) References Cited

U.S. PATENT DOCUMENTS

| 2,822,802 | A  | * | 2/1958 | Corriero ....................... 600/210 |
|---|---|---|---|---|
| 5,728,046 | A  | * | 3/1998 | Mayer et al. .................. 600/210 |
| 5,928,139 | A  | * | 7/1999 | Koros et al. .................. 600/205 |
| 5,944,658 | A  | * | 8/1999 | Koros et al. .................. 600/232 |
| 6,139,493 | A  | * | 10/2000 | Koros et al. ................. 600/215 |
| 6,312,443 | B1 | * | 11/2001 | Stone ............................ 606/198 |
| 6,648,891 | B2 | * | 11/2003 | Kim ............................ 606/86 B |
| 6,749,563 | B2 | * | 6/2004 | Stihl ............................. 600/196 |
| 7,261,688 | B2 | * | 8/2007 | Smith et al. ................... 600/210 |
| 7,494,463 | B2 | * | 2/2009 | Nehls ............................ 600/227 |
| 7,594,888 | B2 | * | 9/2009 | Raymond et al. ............. 600/219 |
| 7,959,564 | B2 | * | 6/2011 | Ritland ......................... 600/201 |
| 2006/0106416 | A1 | * | 5/2006 | Raymond et al. ............. 606/198 |
| 2007/0270655 | A1 | * | 11/2007 | Smith et al. ................. 600/210 |
| 2008/0214898 | A1 | * | 9/2008 | Warren ......................... 600/210 |
| 2009/0270925 | A1 | * | 10/2009 | Aryan ........................... 606/286 |
| 2010/0022844 | A1 | * | 1/2010 | Mangiardi .................... 600/201 |
| 2010/0152781 | A1 | * | 6/2010 | Nehls ............................ 606/280 |
| 2010/0274298 | A1 | * | 10/2010 | Schiff ........................... 606/329 |

* cited by examiner

*Primary Examiner* — Ellen C Hammond
*Assistant Examiner* — Jacqueline Johanas
(74) *Attorney, Agent, or Firm* — Holland & Hart LLP

(57) ABSTRACT

A surgical instrument, generally in the form of an expandable elongate conduit, for use as a distractor and/or retractor. The conduit generally includes a first elongate trough and a second elongate trough movable between an expanded state and a collapsed state wherein the second trough is nestable with the first trough. The first and second troughs may be fastened to vertebrae to facilitate distraction and/or compression of the vertebrae relative to one another.

14 Claims, 7 Drawing Sheets

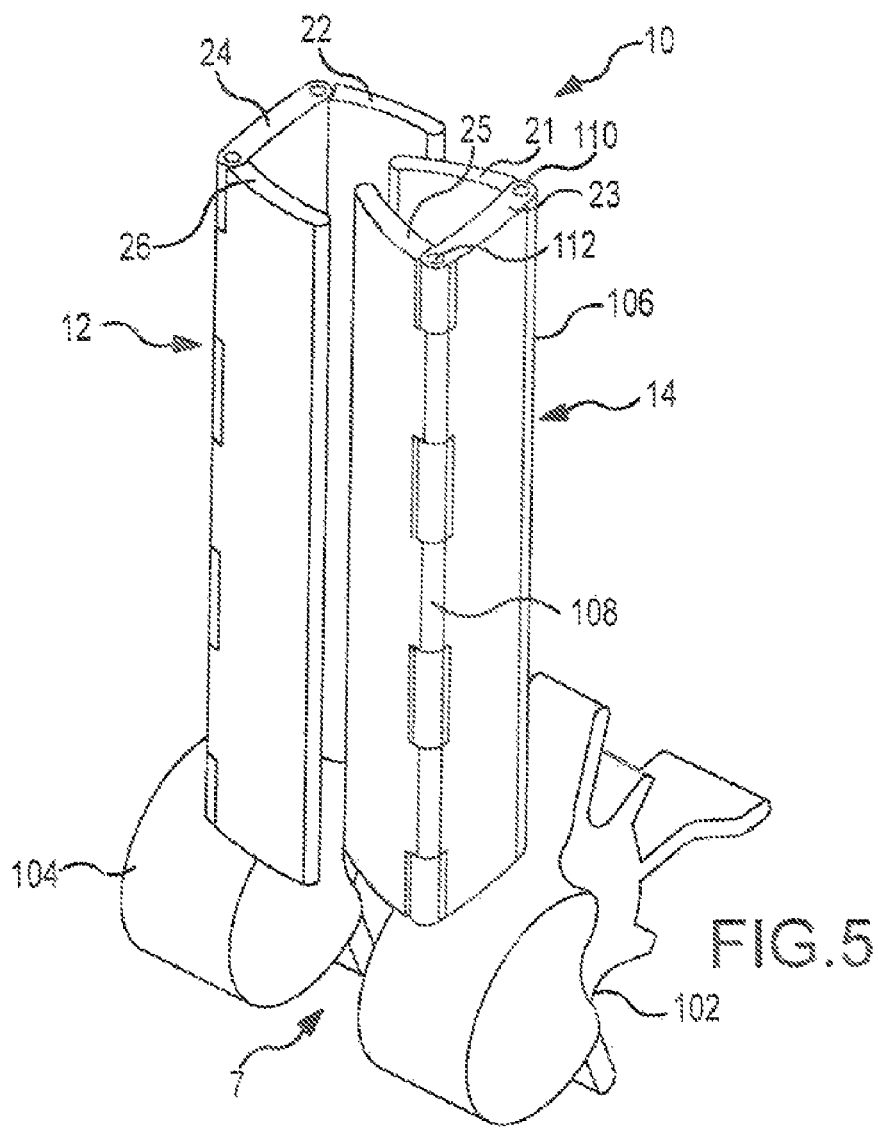
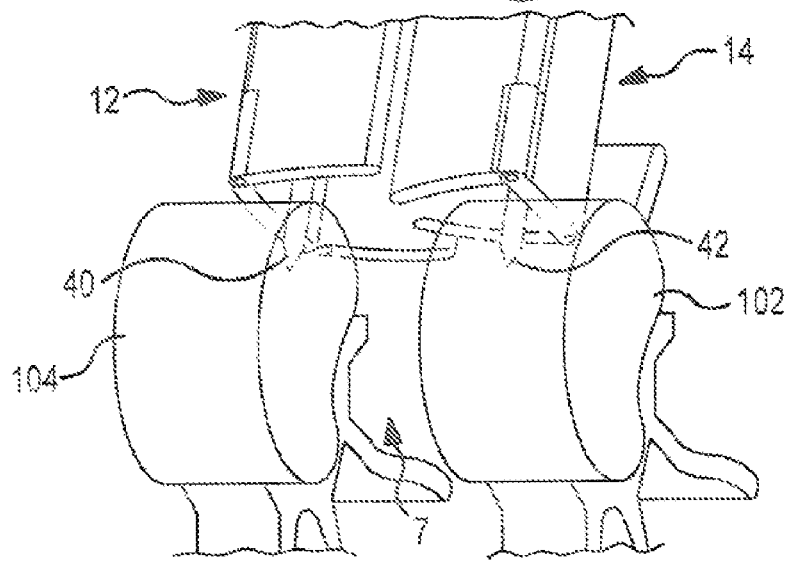

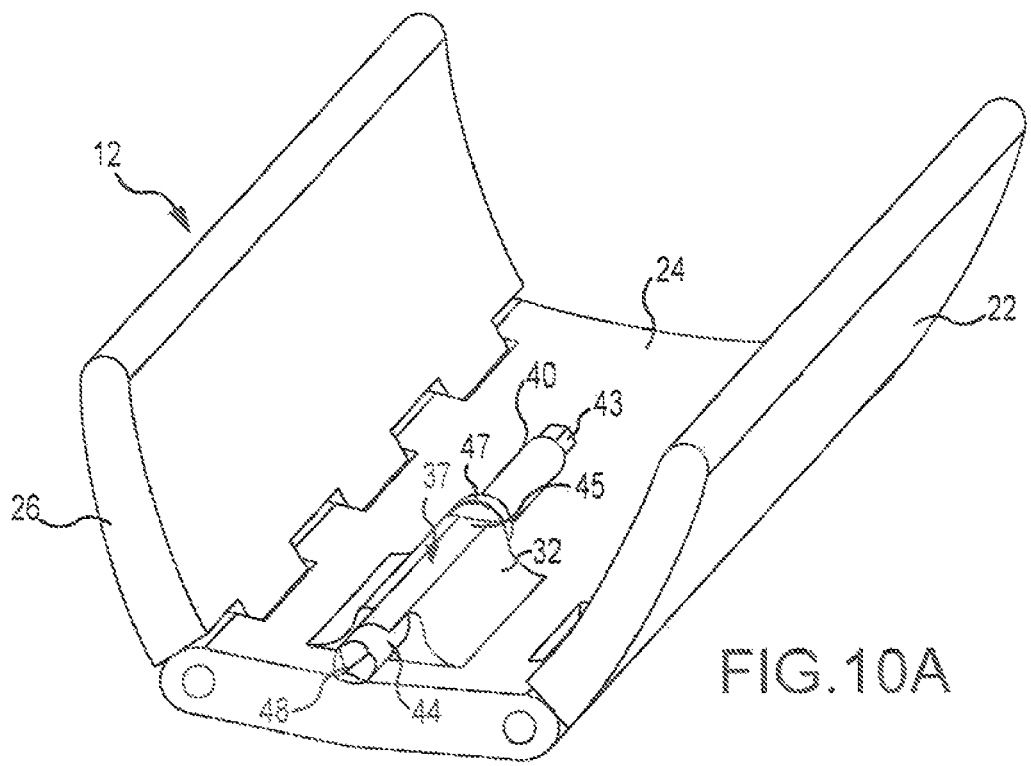
FIG.10A
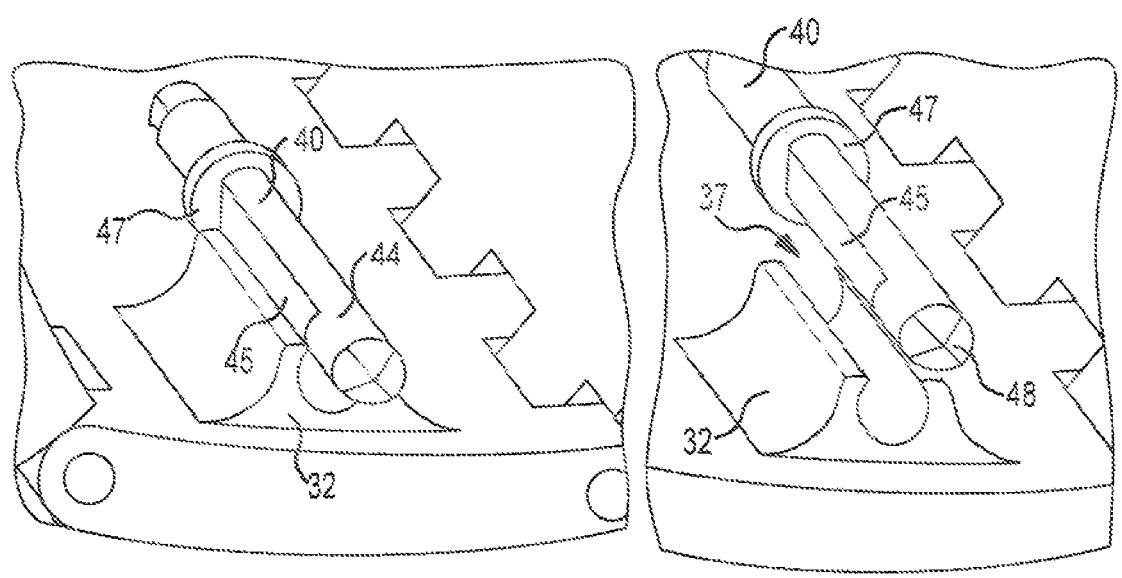
FIG.10B
FIG.10C

EXPANDABLE RETRACTOR AND METHODS INCORPORATING THE SAME

RELATED APPLICATIONS

This application claims priority to U.S. Provisional Patent Application No. 61/168,758, filed Apr. 13, 2009, titled the same and incorporated herein as if set out in full.

BACKGROUND

The vertebrae of the human spine are arranged in a column with one vertebra on top of the next. An intervertebral disc lies between adjacent vertebrae to transmit force between the adjacent vertebrae and provide a cushion between them. The discs allow the spine to flex and twist.

With age, spinal discs begin to break down, or degenerate resulting in the loss of fluid in the discs and consequently resulting in them becoming less flexible. Likewise, the discs become thinner allowing the vertebrae to move closer together. Degeneration may also result in tears or cracks in the outer layer, or annulus, of the disc. The disc may begin to bulge outwardly. In more severe cases, the inner material of the disc, or nucleus, may actually extrude out of the disc.

In a process known as spinal stenosis, the spinal canal may narrow due to excessive bone growth, thickening of tissue in the canal (such as ligamentous material), or both.

The facet joints between adjacent vertebrae may degenerate and cause localized and/or radiating pain.

In addition to degenerative changes in the disc, the spine may undergo changes due to trauma from automobile accidents, falls, heavy lifting, and other activities.

The spine may also be malformed from birth or become malformed over time, such as, for example, in cases of scoliosis, kyphosis, spondylosis, spondylolisthesis, and other deformities.

The conditions described above can result in disfigurement, pain, numbness, weakness, or even paralysis in various parts of the body. All of the above conditions and similar conditions are collectively referred to herein as spine disease.

Typically, surgeons treat spine disease by attempting to stabilize adjacent vertebrae relative to one another and/or restore the normal spacing between adjacent vertebrae to improve the shape of the spine and to relieve pressure on affected nerve tissue. Stabilizing the vertebrae is often accomplished with plates and/or rods attached to the vertebrae with fasteners such as screws, such as, for example, pedicle screws. The stabilization may be rigid such that it eliminates motion between adjacent vertebrae and encourages bony fusion between the vertebrae or it may be dynamic to allow continued motion between the vertebrae. Often the stabilization includes inserting a rigid spacer made of bone, metal, or plastic into the disc space between the adjacent vertebrae and allowing the vertebrae to grow together, or fuse, into a single piece of bone.

Surgical treatment of the spine requires gaining access to the spine and safely introducing instruments and implants into the surgical site. Traditional surgical procedures for the spine can cause significant trauma to the nerves, vessels and other tissues adjacent the spine. While various instruments and techniques to limit the trauma associated with spinal surgery exist, the need for improvement in this area remains.

SUMMARY

Provided herein is a surgical instrument generally in the form of an expandable elongate conduit for use as a distractor/compressor or retractor. The conduit may include a first elongate trough and a second elongate trough movable between an expanded state and a collapsed state wherein the second trough is nestable with the first trough. The first and second troughs may each include a fastener, such as a pin, extendably disposed thereon. The first and second elongate troughs extend along respective first and second elongate axes and the fasteners may be extendable generally parallel to the elongate axes. Each fastener may be disposed on the interior of its respective trough.

The first and second fasteners may each be releasably and rotatably disposed on their respective trough. The first and second fasteners each include an elongate shank portion and each of the first and second troughs may include an elongate slideway adapted to receive a respective fastener. Each of the slideways may include a slit extending along its length, and each shank portion may have a cross-sectional profile configured such that the shank portion may be rotatably aligned with a respective slit whereby the fastener may be released from its respective trough.

In another example, the trough may include a plurality of panels pivotably joined to each other and movable between a collapsed state and an expanded state wherein the first and second troughs cooperate to form a conduit therebetween. The trough may include three panels, one of which may be arcuate in shape. Also, it may be desirable to resiliently bias the troughs toward the expanded state. The panels may be hingedly joined to each other and may be comprised of plastic or metal.

Also contemplated is a method for distracting or compressing adjacent vertebrae including inserting an expandable conduit proximate the adjacent vertebrae, wherein the conduit comprises first and second troughs. Each of the first and second troughs includes an extendable fastener. The fasteners are extended into adjacent vertebrae thereby temporarily securing each trough to an associated one of the adjacent vertebrae. The conduit is expanded by urging the first and second troughs away from each other wherein the adjacent vertebrae are distracted from each other. Likewise, the troughs may be urged together to compress the vertebrae. The fasteners may be disengaged from the troughs in order to remove the troughs with the fasteners still in place. The fasteners may be urged apart or together independently of the troughs to distract or compress the vertebrae. The fasteners may be used to guide placement of a bone plate on the vertebrae.

BRIEF DESCRIPTION OF THE DRAWINGS

The accompanying drawings, which are incorporated in and constitute a part of this specification, illustrate embodiments of the present invention and together with the description, serve to explain the principles thereof. Like items in the drawings are referred to using the same numerical reference.

FIG. 5 is a perspective view of the retractor shown moving between the collapsed state and an expanded state;

FIG. 6 is an enlarged partial perspective view of the retractor taken from the front illustrating the distraction of adjacent vertebrae;

FIG. 10A is an enlarged partial perspective view of a fastener attached to a first portion of the retractor;

FIG. 10B is an enlarged partial perspective view of the fastener partially disengaged from the first portion of the retractor;

FIG. 10C is an enlarged partial perspective view of the fastener fully disengaged from the first portion of the retractor.

DETAILED DESCRIPTION

Figure 1:
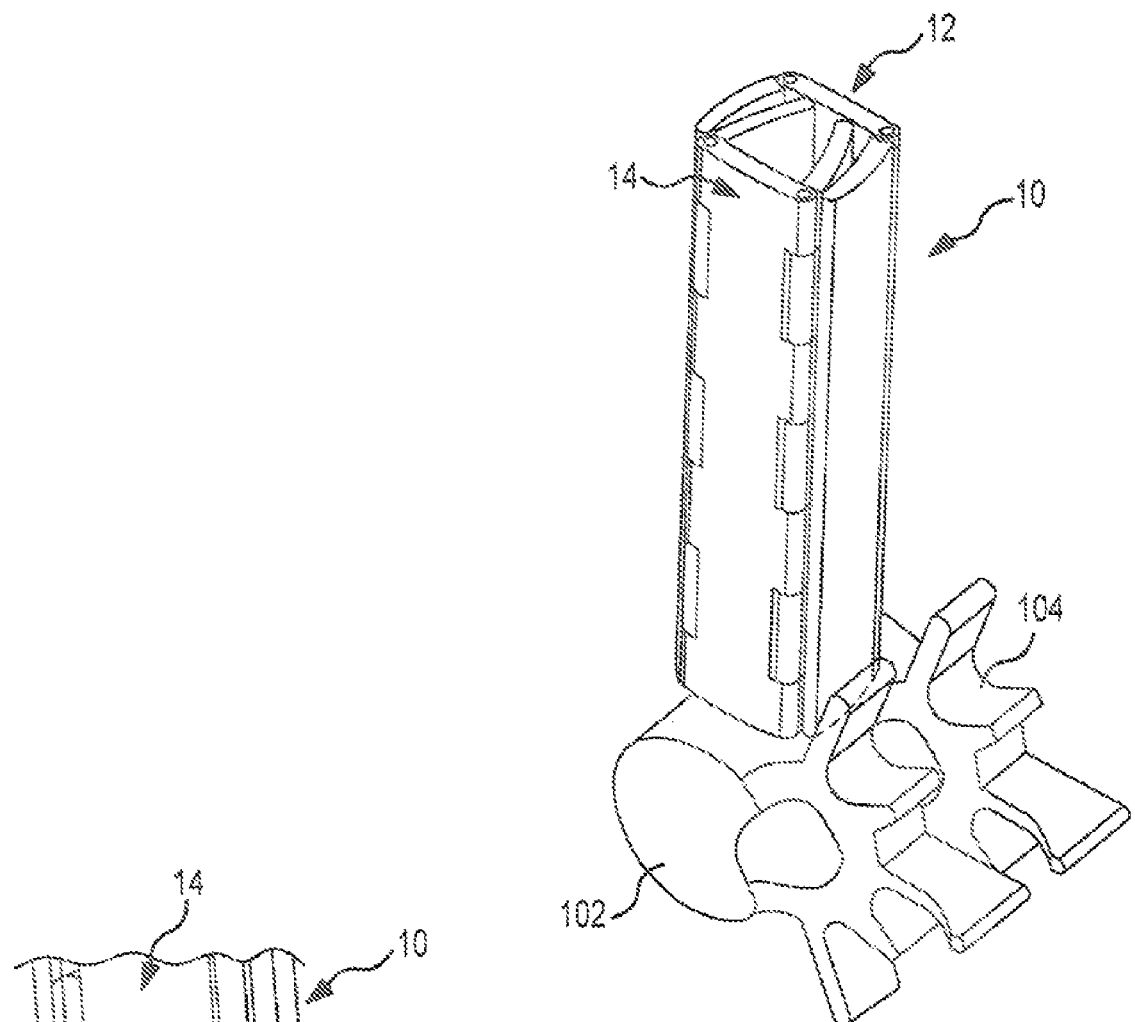
FIG. 1 is a perspective view of an expandable retractor according to an exemplary embodiment showing the retractor in a collapsed state.
Figure 2:
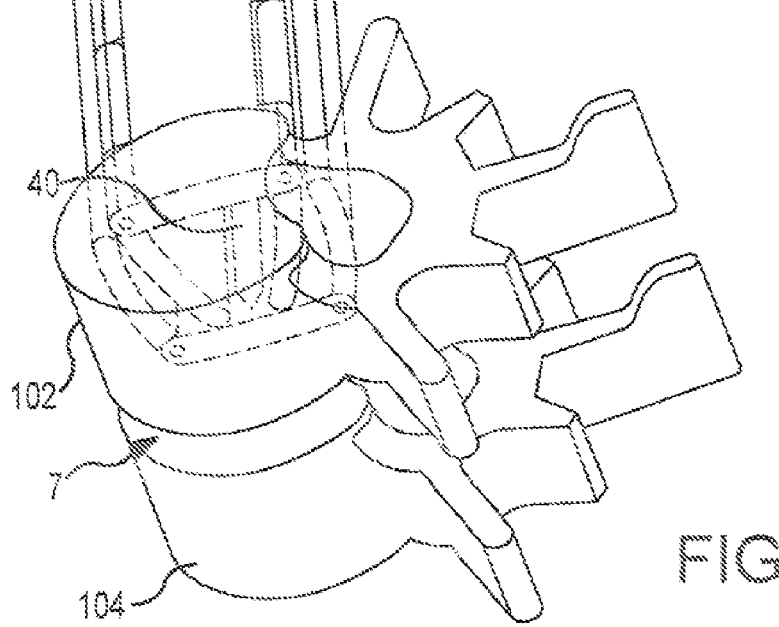
FIG. 2 is an enlarged partial perspective view taken from below of the retractor shown in FIG. 1.

FIG. 1 illustrates an exemplary embodiment of an expandable retractor 10 that has been placed proximate to adjacent vertebrae 102 and 104. Retractor 10 includes first and second elongate portions shown as generally "U"-shaped elongated troughs 12 and 14 respectively. With further reference to FIG. 2, it may be appreciated that adjacent vertebrae 102 and 104 are separated by an intervertebral space 7, which is ordinarily occupied by an intervertebral disc. When an intervertebral disc is damaged and surgery is undertaken to correct the damage, vertebrae 102 and 104 may be separated, or distracted, in order to allow access for tools, implants, and the like. In addition, surrounding tissue must be retracted to prevent unnecessary trauma. Vertebrae 102 and 104 may be moved together or compressed, for example, to abut an implant. The expandable retractor 10, as described herein, acts as a distractor/compressor for separating or compressing vertebrae as well as a retractor for providing clear access to intervertebral space 7 and protecting surrounding tissue from cutting tools. Again, referring to FIGS. 1 and 2, it may be appreciated that retractor 10 is in a collapsed state wherein second elongate trough 14 is nested with elongate trough 12. Also shown in FIG. 2 is a fastener 40, shown here in the retracted state.

Figure 3:
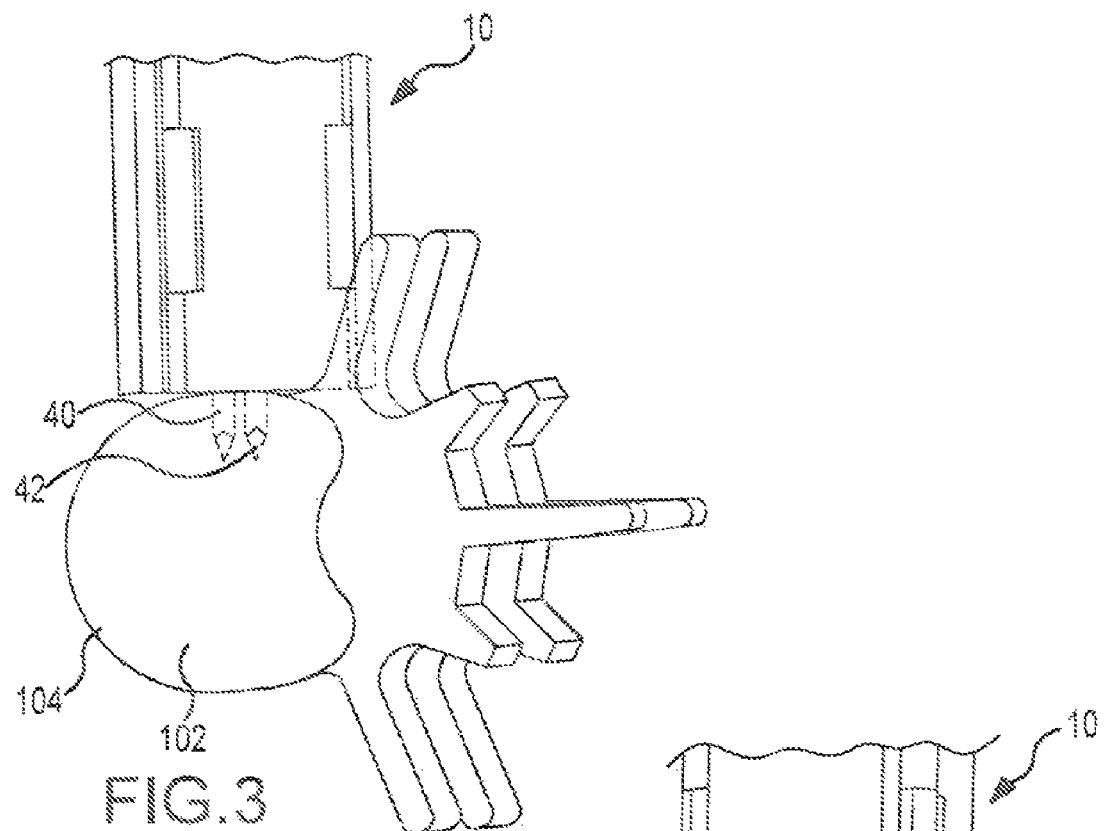
FIG. 3 is an enlarged partial perspective view taken from the side of the retractor shown with the fasteners extended and engaging adjacent vertebrae.
Figure 4:
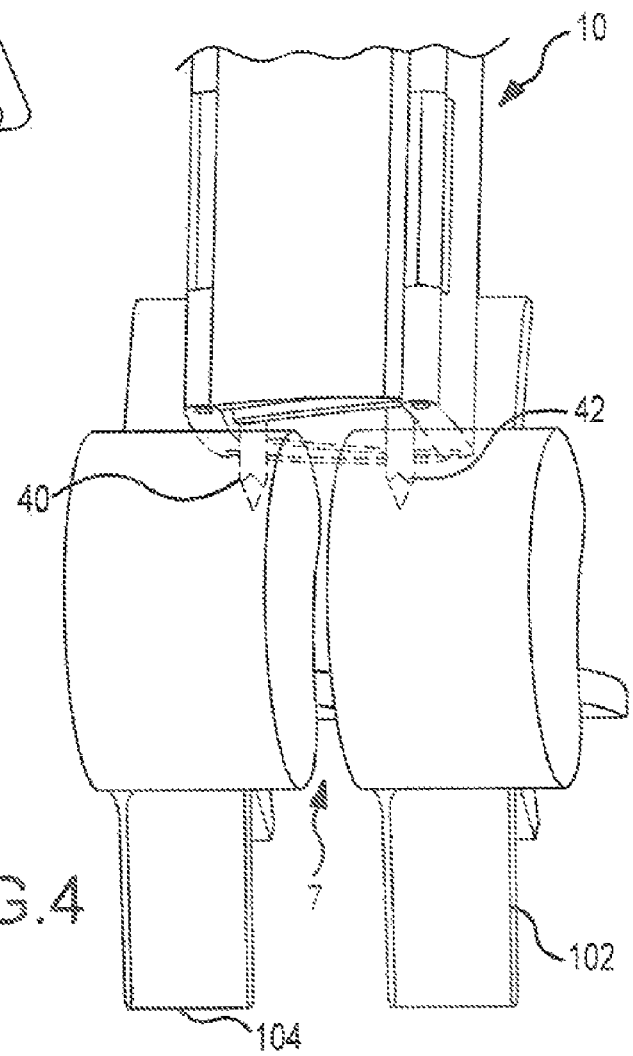
FIG. 4 is an enlarged partial perspective view taken from the front of the retractor shown with the fasteners extended and engaging adjacent vertebrae.

Now referring to FIGS. 3 and 4, it can be seen that fasteners 40 and 42 have been extended into the vertebral bodies of corresponding vertebrae 102 and 104. In this case, fasteners 40 and 42 are in the form of elongate pins, which may be driven into the vertebral bodies. Thus, retractor 10 is anchored to the adjacent vertebrae. It should be understood that fasteners 40 and 42 could have a different configuration such as screw threads or the like.

Figure 7:
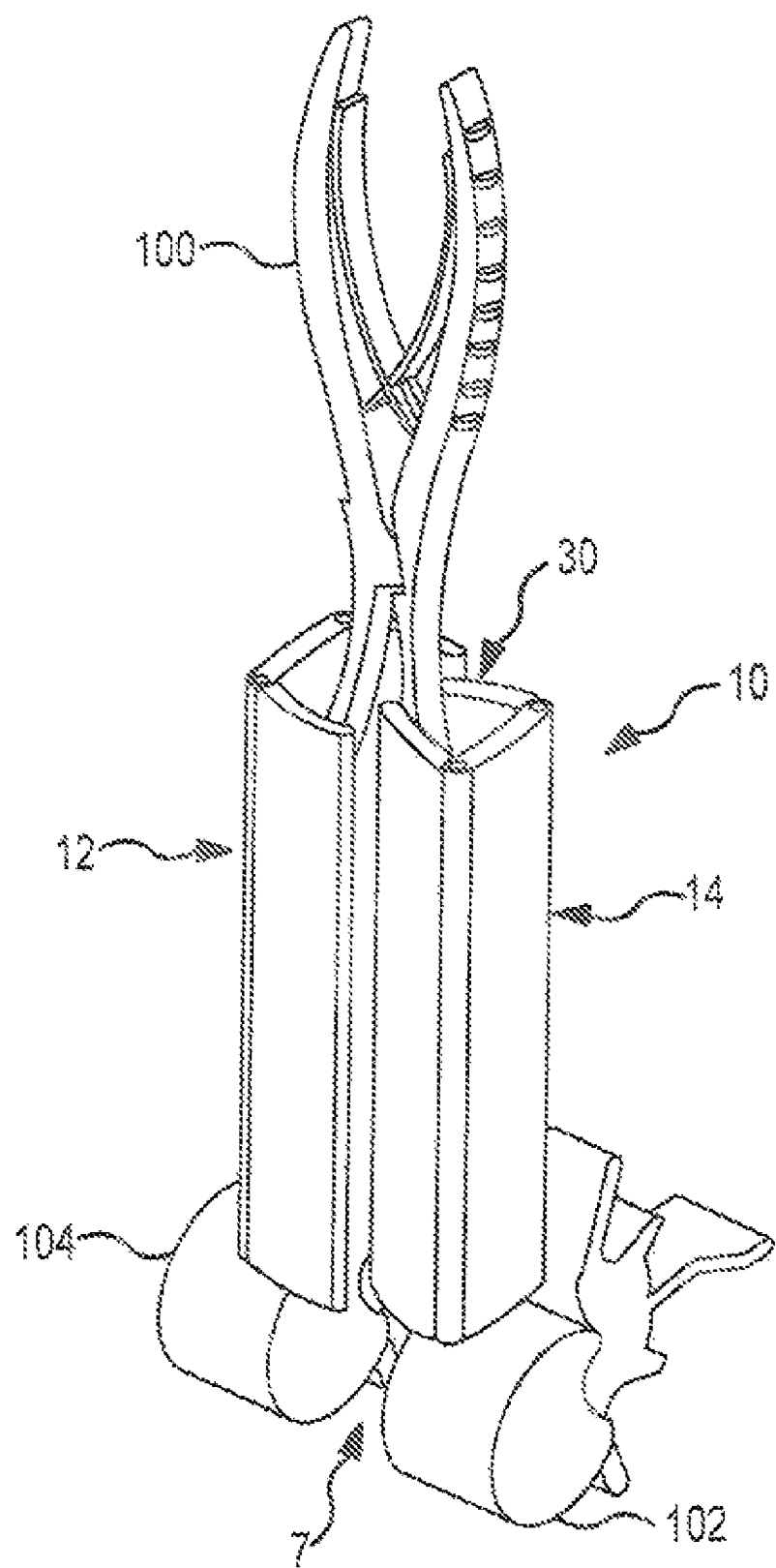
FIG. 7 is a perspective view of first and second portions of the retractor being urged apart with a secondary distraction instrument.

Referring to FIGS. 5 and 6, it can be seen that once elongate troughs 12 and 14 are anchored to adjacent vertebrae 102 and 104, retractor 10 may be expanded by urging first and second troughs 12 and 14 away from each other. Accordingly, as troughs 12 and 14 are urged apart, vertebrae 102 and 104 are also urged apart or distracted. Thus, space 7 is enlarged providing more space for a surgical procedure to be performed and/or restoring the vertebrae to more natural spacing. Furthermore, soft tissues surround the wound through which the troughs 12 and 14 pass are also urged apart or retracted by the trough walls. As shown in FIG. 5, trough 12 is in an expanded state while trough 14 is shown in a collapsed or partially collapsed state. As shown in FIG. 7, in some embodiments troughs 12 and 14 may be urged apart with a secondary distraction instrument, such as a spreader 100. Spreader 100 is generally known in the art and will not be further explained herein. Other suitable distraction instruments known in the art also may be employed to expand retractor 10.

In the illustrative example, elongate troughs 12 and 14 include a plurality of panels, which are hinged or otherwise moveably connected to each other. For example, first elongate trough 12 includes panels 22, 24, and 26. Similarly, second elongate trough 14 includes panels 21, 23, and 25. These panels are hinged together with hinges 106 and 108. Each hinge 106 and 108 includes a respective hinge pin 110 and 112 about which the panels rotate. The exact construction of these hinges may vary. For example, in one embodiment at least one of the troughs 12, 14 is formed of plastic sufficiently flexible to allow troughs 12, 14 to collapse and expand as described above. Furthermore, the hinges may comprise sections of plastic that are thin relative to the panels, thereby acting as hinges. To prevent tissue from interfering with hinges 106 and 108, it may be necessary to use a sheath or shield (not shown in Figures) around the retractor 10. The sheath or shield may be expandable and contractible.

In some embodiments, first elongate trough 12 could be a rigid trough without hinges. As such, second elongate trough 14, being collapsible by virtue of its hinged panels 21, 23, and 25, would still be able to nest with trough 12. Furthermore, each trough could include a lesser or greater number of panels than shown in the Figures. Also, troughs 12 and 14 could be in the form of arcuate troughs of unitary construction that nest together. Troughs 12 and 14 could each be formed of a resilient material shaped as a trough, such as the shape of trough 12 as shown in FIG. 5. Troughs 12 and 14 may be comprised of any suitable material such as plastic or metal. In a particular embodiment, the nestled trough 12 or 14 comprises a resilient material that biases the trough towards the expanded position. In this manner, the trough material aids in creating a channel through the tissue to the operative site (e.g., to disc space 7).

Figure 8:
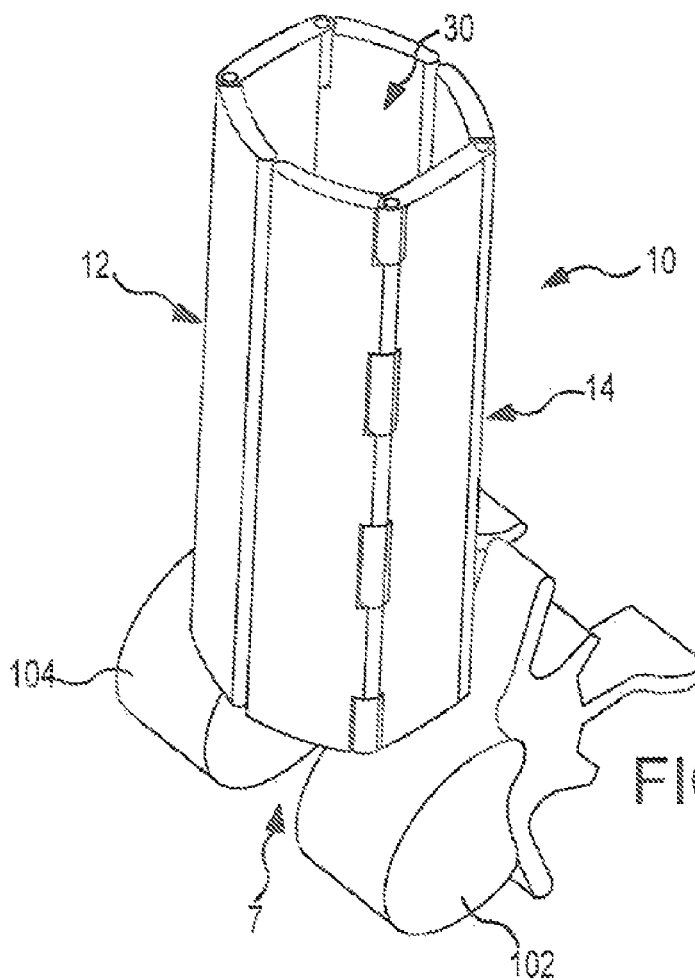
FIG. 8 is a perspective view of the retractor shown in the expanded state.
Figures 9A, 9B:
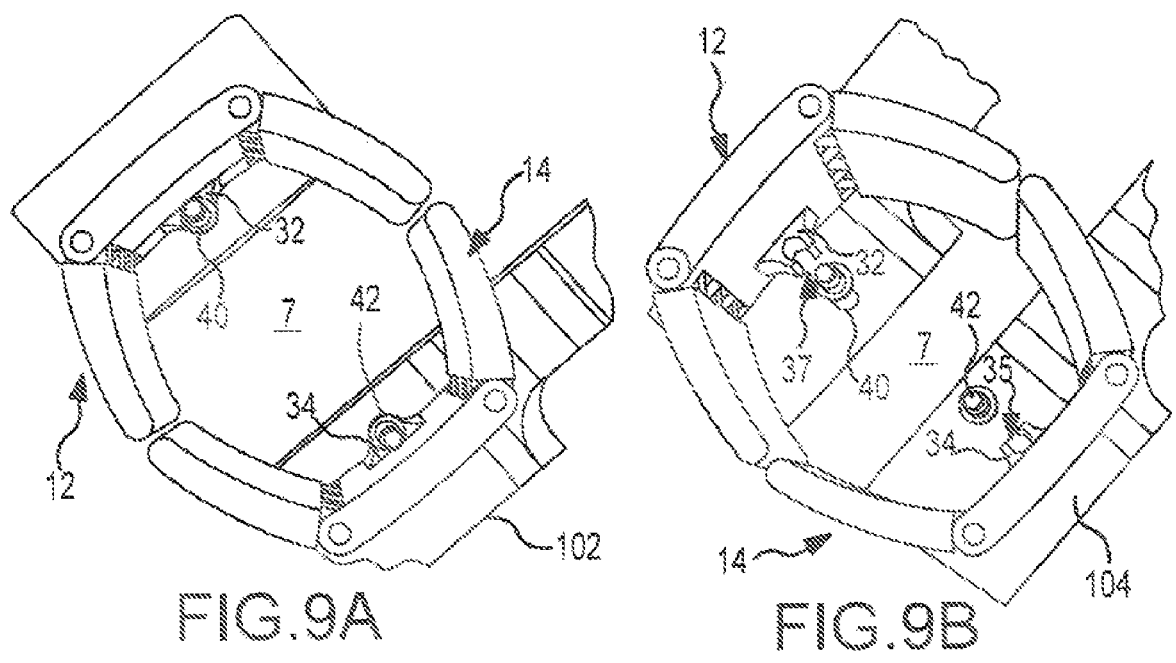
FIG. 9A is a top down view of the retractor showing fasteners attached to the first and second portions of the retractor.
FIG. 9B is a top down view of the retractor showing the fasteners disengaged from the first and second portions of the retractor.

Referring now to FIG. 8, retractor 10 has been urged apart and elongate trough 14 is in an expanded state such that troughs 12 and 14 cooperate to provide a conduit opening 30 that provides access to intervertebral space 7. Comparing FIG. 9A with FIG. 9B, it can be appreciated that fasteners 40 and 42 may be disengaged from their respective troughs. Accordingly, troughs 12 and 14 may be further expanded as shown in FIG. 9B or even removed from the patient while leaving fasteners 40 and 42 in place to act as datum points for subsequent preparation or procedures, such as installing a bone plate.

Referring to FIGS. 10A-10C, in some embodiments fastener 40 is slidably and rotatably disposed in a slideway 32. Slideway 32 may be integrally formed with panel 24 on the interior of trough 12. Fastener 40 includes an elongate shank portion 44 including a profile 45 (for example, a flattened portion) that when rotated is alignable with an opening 37, shown in FIGS. 10A-10C as a slit 37. Slit 37 extends along the length of slideway 32. Referring specifically to FIG. 10A, fastener 40 is rotated such that profile 45 does not align with slit 37. Accordingly, fastener 40 is secured to panel 24. In this position, fastener 40 may be extended or retracted as necessary by sliding the fastener 40 longitudinally within the slideway 32 to secure trough 12 to the vertebra. Referring now to FIG. 10B, it can be seen that fastener 40 is rotated such that profile 45 aligns with slit 37 allowing fastener 42 to disengage from slideway 32. FIG. 10C is similar to FIG. 10B; however, fastener 40 is further disengaged from slideway 32. In an alternative embodiment, slideway 32 is disposed within a wall, or a portion of a wall, of panel 24 instead of on the inner surface of panel 24.

Fastener 40 may include a polygonal head 43 to facilitate rotation of fastener 40. In this embodiment, an instrument such as a driver is coupled to head 43 to facilitate rotation of fastener 40. Fastener 40 may be rotated using other means, such as, for example, a polygonal socket formed into the fastener. Fastener 40 also includes a sharp point 48 to ease the extension of the fastener 40 into the vertebra. A flange 47 is disposed along shank 44 and captures slideway 32, thereby fastening trough 12 to the vertebrae when fastener 40 is extended into the vertebral body. Fastener 42 and its associated slideway 34 and slit 35 are substantially similar to fastener 40 and slideway 32.

Figure 11:
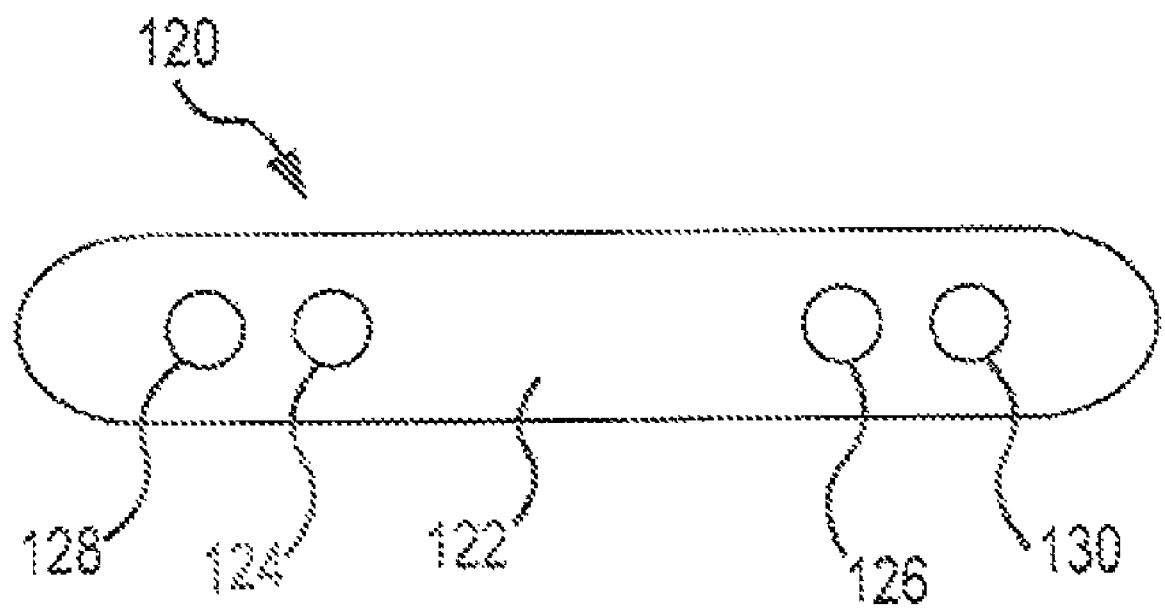
FIG. 11 is a top plan view of a bone plate.

FIG. 11 illustrates a bone plate 120 having a body 122, first and second guide holes 124 and 126, and first and second fixation holes 128 and 130. Guide holes 124 and 126 are engageable with fasteners 40 and 42 to locate the plate 120 on the vertebrae. Fixation members, such as screws (not shown), are insertable into fixation holes 128 and 130 to affix the plate 120 to the vertebrae.

Methods relating to the above described expandable retractor are also contemplated. The methods, thus, encompass the steps inherent in the above described mechanical structures. Broadly, one method for distracting adjacent vertebrae includes inserting an expandable conduit proximate the adjacent vertebrae. The conduit includes first and second troughs each including an extendable fastener. Once the conduit is inserted, the fasteners are extended into adjacent vertebrae, thereby temporarily securing each trough to an associated vertebrae. The conduit is then expanded by urging the first and second troughs away from each other, thereby distracting or urging apart the adjacent vertebrae. Once the procedure has been completed, or preparation of the vertebrae has been completed, the fasteners are disengaged from the troughs and the troughs are expanded or removed and a plate optionally located using the fasteners 40 and 42 as datum guides.

Accordingly, the present invention has been described with some degree of particularity directed to the exemplary embodiments. It should be appreciated, though, that the present invention is defined by the following claims construed in light of the prior art so that modifications or changes may be made to the exemplary embodiments without departing from the inventive concepts contained herein.

What is claimed is:

1. A surgical instrument, comprising:
a first elongate trough movable between an expanded state and a collapsed state including a first fastener extendably disposed thereon; and
a second elongate trough movable between an expanded state and a collapsed state wherein said second trough is nestable with said first trough, said second elongate trough including a second fastener extendably disposed thereon;
wherein said first and second elongate troughs extend along respective first and second elongate axes and said first and second fasteners are extendable generally parallel to respective said first and second elongate axes;
wherein said first and second fasteners are each releasably disposed on their respective said trough;
wherein each of said first and second fasteners are each rotatably disposed on their respective said trough;
wherein each of said first and second fasteners includes an elongate shank portion and each of said first and second troughs includes an elongate slideway adapted to receive a respective said fastener;
wherein each of said slideways includes a slit extending along its length, and wherein each said shank portion has a cross-sectional profile configured such that said shank may be rotatably aligned with a respective said slit whereby said fastener may be released from its respective said trough.

2. A surgical instrument according to claim 1 wherein at least one of said first and second fasteners is disposed on an interior of its respective said trough.

3. A surgical instrument according to claim 1 wherein each of said fasteners is a pin.

4. A surgical instrument, comprising:
a first elongate trough including a first extendable fastener; and
a second elongate trough including a second extendable fastener, and including a plurality of panels pivotably joined to each other and movable between a collapsed state wherein said second trough is nestable with said first trough and an expanded state wherein said first and second troughs cooperate to form a conduit therebetween.

5. A surgical instrument according to claim 4 wherein said second elongate trough includes three panels.

6. A surgical instrument according to claim 5 wherein at least one of said panels is arcuate.

7. A surgical instrument according to claim 4 wherein said first elongate trough is movable between a collapsed state and an expanded state.

8. A surgical instrument according to claim 4 wherein said second trough is resiliently biased toward the expanded state.

9. A surgical instrument according to claim 4 wherein each of said fasteners includes an elongate shank portion and each of said first and second troughs includes an elongate slideway adapted to receive a respective said fastener.

10. A surgical instrument according to claim 4 wherein said panels are hingedly joined to each other.

11. A surgical instrument according to claim 10 wherein said second elongate trough is comprised of metal.

12. A surgical instrument according to claim 4 wherein said second elongate trough is comprised of plastic.

13. A method for distracting adjacent vertebrae, comprising:
inserting an expandable conduit proximate the adjacent vertebrae, wherein said conduit comprises first and second troughs, each said first and second trough including an extendable fastener;
extending said fasteners into adjacent vertebrae thereby temporarily securing each said trough to an associated one of said adjacent vertebrae;
expanding the conduit by urging said first and second troughs away from each other wherein the adjacent vertebrae are distracted from each other;
rotating each of said fasteners relative to its respective said trough in order to disengage said fasteners from said troughs;
disengaging said fasteners from said troughs; and
removing said troughs.

14. A method for distracting adjacent vertebrae according to claim 13 including after disengaging said fasteners from said troughs, guiding the placement of a bone plate on said adjacent vertebrae with said fasteners.

\* \* \* \* \*